United States Patent [19]

Hiller et al.

[11] Patent Number: 4,559,207
[45] Date of Patent: Dec. 17, 1985

[54] REACTOR FOR PRODUCING METHANOL AND PROCESS

[75] Inventors: Heinz Hiller, Offenbach; Emil Supp, Dietzenbach; Friedemann Marschner, Weisskirchen; Hans Küpfer, Frankfurt am Main; Lutz Weidemann, Steinbach, all of Fed. Rep. of Germany

[73] Assignee: Metallgesellschaft AG, Frankfurt am Main, Fed. Rep. of Germany

[21] Appl. No.: 555,860

[22] Filed: Nov. 28, 1983

Related U.S. Application Data

[63] Continuation of Ser. No. 320,800, Nov. 12, 1981, abandoned, which is a continuation of Ser. No. 726,339, Sep. 24, 1976, abandoned, which is a continuation of Ser. No. 521,821, Nov. 7, 1974, abandoned, which is a continuation of Ser. No. 297,141, Oct. 12, 1972, abandoned.

[30] Foreign Application Priority Data

Oct. 27, 1971 [DE] Fed. Rep. of Germany ....... 2153437

[51] Int. Cl.[4] ............................ B01J 8/06; B01J 19/02
[52] U.S. Cl. ..................................... 422/197; 422/201; 422/240; 422/241; 422/312; 518/712; 518/713
[58] Field of Search ............... 422/197, 201, 240, 241, 422/312; 75/124 F, 128 R; 518/712, 713

[56] References Cited

U.S. PATENT DOCUMENTS

| | | | |
|---|---|---|---|
| 1,440,109 | 12/1922 | Schenck | 422/241 |
| 1,909,358 | 5/1933 | Jaeger | 422/197 |
| 1,934,836 | 11/1933 | Wietzel et al. | 422/197 X |
| 2,308,307 | 1/1943 | Robinson | 138/140 |
| 2,354,163 | 7/1944 | Weizmann et al. | 422/241 X |
| 2,632,528 | 3/1953 | Berg et al. | 518/722 X |
| 2,662,911 | 12/1953 | Dorschner et al. | 518/712 |
| 3,152,934 | 10/1964 | Lula et al. | 75/124 F X |
| 3,326,956 | 6/1967 | Davies et al. | 518/713 |
| 3,449,802 | 3/1970 | Lagneborg | 75/128 R X |
| 3,959,177 | 5/1976 | Martin | 422/15 X |
| 4,119,765 | 10/1978 | Pinnola et al. | 428/683 |
| 4,405,389 | 9/1983 | Larson | 75/128 V X |

FOREIGN PATENT DOCUMENTS

| | | | |
|---|---|---|---|
| 0454428 | 9/1936 | United Kingdom | 422/241 |
| 1159035 | 7/1969 | United Kingdom | 518/713 |
| 1205156 | 9/1970 | United Kingdom | 518/713 |
| 1245587 | 9/1971 | United Kingdom | 518/713 |

OTHER PUBLICATIONS

Shell Dev. Comp. Corrosion Data Survey, 1954 ed., p. C-3.
Guy: Elements of Physical Metallury, 1967, pp. 385-390.
Kirk–Othmer, Encyclopedia of Chemical Technology, 2nd ed., vol. 13, pp. 386-388.
Kirk–Othmer, Encyclopedia of Chemical Technology, 2nd ed, vol 18, pp. 789-794.

*Primary Examiner*—Barry S. Richman
*Assistant Examiner*—B. P. Heaney
*Attorney, Agent, or Firm*—Sprung Horn Kramer & Woods

[57] ABSTRACT

A reactor is provided for producing methanol by the reaction of synthesis gases containing carbon oxides and hydrogen in contact with a copper containing catalyst positioned in the reactor in catalyst tubes surrounded by boiling water under pressure. The catalyst tubes are made from a metallic material which is catalytically inactive with respect to the methanol synthesis gas and have approximately the same coefficient of thermal expansion as the shell of the reactor. The catalyst tubes are made of a steel composed of mixed austeniticferritic structure and containing 10–30% by weight chromium.

1 Claim, 3 Drawing Figures

REACTOR FOR PRODUCING METHANOL AND PROCESS

This is a continuation of application Ser. No. 320,800 filed Nov. 12, 1981, now abandoned, which is a continuation of Ser. No. 726,339 filed Sept. 24, 1976 now abandoned, which is a continuation of Ser. No. 521,821 filed Nov. 7, 1974, now abandoned, which is a continuation of Ser. No. 297,141 filed Oct. 12, 1972, now abandoned.

BACKGROUND

This invention relates to an improved reactor and process for producing methanol utilizing catalyst tubes which are catalytically inert with respect to the methanol synthesis gases and have approximately the same thermal expansion properties as the reactor in which the methanol synthesis is carried out. It is known to produce methanol by the reaction of a synthesis gas, which contains oxides of carbon, and hydrogen, in contact with catalysts which contain zinc and chromium and under pressures above 300 kilograms per square centimeter above atmospheric pressure and at temperatures of about 320°–400° C. The reactors used for this purpose are cylindrical pressure vessels, in which the catalyst packing is divided into a plurality of layers. Cold fresh synthesis gas and/or cooled recycled synthesis gas is introduced between the catalyst layers so that the heat of reaction is partly consumed. Owing to the high reaction pressure, considerable energy is required to compress the synthesis gas. If the synthesis gas is available under a pressure of 16 kilograms per square centimeter, about 408 kWh are required per metric ton of methanol product for the compression to the synthesis pressure of 325 kilograms per square centimeter above atmospheric pressure.

In contact with copper-containing catalysts, synthesis gases having the above-mentioned composition can be reacted to form methanol with good yields under lower pressures and at lower temperatures.

It is known to perform the reaction in contact with catalysts which contain copper, zinc, and, if desired, chromium under pressures of 50–120 kilograms per square centimeter and at temperatures of 230°–280° C. In that case too, shaft reactors are used, in which the catalyst layer is divided and cold gas is introduced between the layers. The compression of the synthesis gas from 16 kilograms per square centimeter above atmospheric pressure to the working pressure of 100 kilograms per square centimeter above atmospheric pressure still requires an energy of 302 kWh per metric ton of methanol product.

It is known to effect the synthesis of methanol in contact with copper-containing catalysts and at the lower reaction pressure and temperature conditions in tubular reactors, in which the catalyst is disposed in tubes which are surrounded by boiling water under pressure. This arrangement of the catalyst results in a very favorable temperature control of the highly exothermic reaction, and the entire heat of reaction is utilized in the production of highpressure steam under a pressure of 35–50 kilograms per square centimeter above atmospheric pressure. If this high-pressure steam is used to drive the compressors for compressing the fresh synthesis gas and/or the recycled synthesis gas, only 54 kWh of extraneous energy are required per metric ton of methanol for the compression.

Some by-products are formed in the synthesis of methanol. In addition to water, these are mainly dimethyl ether, methyl formate, iron carbonyl, higher alcohols and also higher hydrocarbons. The crude methanol produced in the synthesis is purified in most cases by a two-stage distillation. In a first column for the first runnings, those impurities which have a lower boiling point than methanol are distilled off as an overhead product, and in a second, pure methanol column the pure methanol is distilled off as an overhead product from the bottoms product of the first column whereas the higher-boiling impurities remain back as bottoms product.

It has been found that the formation of these by-products is due only in part to the catalyst and particularly the formation of hydrocarbons is due to the catalytic activity of the reactor wall. Specifically, it has been found that the formation of just these by-products is promoted in tubular reactors in which the catalyst is disposed in tubes that are surrounded by a coolant, and depends much more on the properties of the selected tube material than in shaft reactors. In a tubular reactor there is a much smaller relation of the volume to the surface of the catalyst layer. When these tubes are made from plain carbon steel or low-alloy carbon steels, which have proved quite satisfactory as a material for shaft reactors, up to more than 2000 ppm hydro-carbons may be found in the methanol product. These hydrocarbons include compounds having a boiling range near the boiling point of the methanol so that their separation from methanol by distillation involves a high expenditure. This disadvantage detracts substantially from the advantage of the water-cooled tubular reactor for the methanol synthesis these advantages reside in the highly effective dissipation of the heat of reaction and in the ability to produce high-pressure steam. It must also be borne in mind that the tubular reactor is more complicated in structure than the simple shaft reactor so that in addition to the catalytic activity, a plurality of other properties of the material must also be taken into account, particularly the coefficient of thermal expansion and the resistance to corrosion by boiling water, which may contain ions.

SUMMARY

This invention relates to a reactor for producing methanol by a reaction of synthesis gases which contain oxides of carbon, and hydrogen, in contact with a copper-containing catalyst which is disposed in the reactor in tubes surrounded by boiling water under pressure.

The reactor according to the invention is characterized in that the tubes which contain the catalyst are made from a metallic material which is catalytically inactive with respect to the synthesis gas and has approximately the same coefficient of thermal expansion as the reactor shell.

DESCRIPTION OF THE DRAWING

In the accompanying drawing

DESCRIPTION

Figure 1:
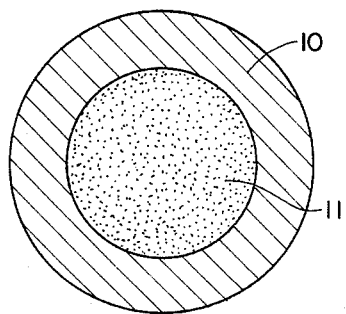
FIG. 1 is a cross-sectional view of a catalyst tube 10 with catalyst 11 which can be used in the present invention.
Figure 2:
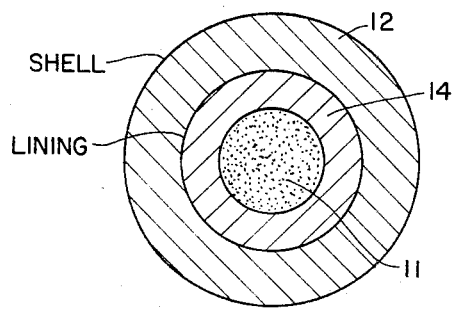
FIG. 2 is a cross-sectional view of a composite catalyst tube having a shell 12 and a lining 14 which can also be used in the invention in an alternate embodiment.
Figure 3:
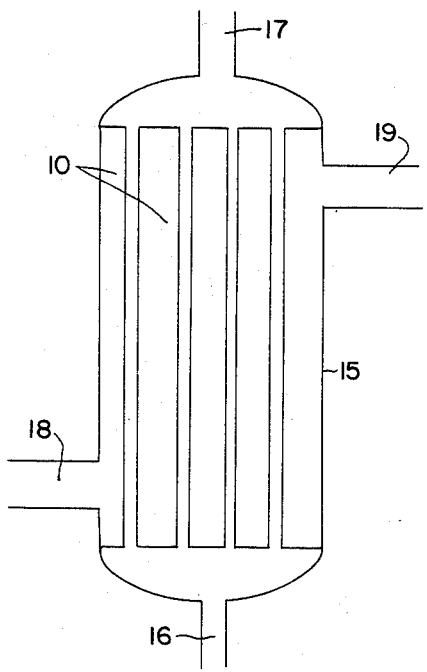
FIG. 3 is a view of a reactor 15 containing a plurality of the catalyst tubes 10 of the present invention, wherein 16 is the synthesis gas inlet, 17 is the product gas outlet, 18 is an inlet for boiling water under pressure and 19 is an outlet for steam.

Metallic materials from which the catalyst tubes may be made in accordance with the invention may be homogeneous or composite materials. The homogeneous materials must be stainless steels because it has been found that even small amounts of iron oxides, i.e., slight rust coatings, will greatly increase the catalytic activity of the inside surface of the tube as regards the formation of hydrocarbons from the methanol synthesis gas.

Steels having a high austenite content, e.g., an austenitic material containing 0.1% by weight C, 18% by weight Cr, 10% by weight Ni (Material No. 1.4541 according to DIN 17007) have virtually no catalytic activity on a gas which contains CO and $H_2$. On the other hand, they can hardly be used in a reactor structure because they have a much higher coefficient of thermal expansion than the plain carbon steels which are conventionally used in the reactor shell. This would result in a complicated and expensive reactor structure. Besides, they are susceptible to stress corrosion if chlorine ions are contained in the water which surrounds the reactor tubes.

Low-carbon chromium steels meet in most cases the requirements as regards catalytic activity and thermal expansion. Steel having a mixed ferritic-austenitic structure and a comparatively lower chromium content may also be used to make the catalyst tubes. Their catalytic activity is very low, and they can be combined well with the plain carbon steels conventionally used as material for the reactor shell.

Alternatively, the catalyst tubes may comprise a shell tube of steel, which is lined on the inside with a material having no catalytic activity, e.g., a cladding of copper or a copper alloy. Such composite materials afford a considerable latitude in the selection of the materials of the reactor shell and the catalyst tubes which may be combined.

Suitable materials are particularly chromium steels and steels having a mixed ferritic-austenitic structure and a chromium content of 10-30% by weight, preferably 13-17% by weight. These steels have a carbon content below 0.15% by weight. Additional alloying constituents may be Ni, Mn, Si, Mo, Zr, and Ti or Nb/Ta may be added as stabilizer (Material No. $\times$3CrNi 1805 according to DIN 17006).

If the catalyst-holding tubes consist of composite materials, the shell tubes may consist of plain carbon steels which need not be stainless nor catalytically inactive. In selecting these steels, it is important that the steel can be lined and approximates the reactor shell material in thermal expansion. Examples of steels which can be lined, e.g., with copper are, e.g., those of Type St 35.8 containing 0.17% by weight C, 0.25% by weight Si, and 0.5% by weight Mn, or of Type 15 Mo 3 containing 0.15% by weight C, 0.25% by weight Si, 0.7% by weight Mn, and 0.3% by weight Mo (Materials No. 1.0061 and No. 1.5415 according to DIN 17007).

The advantages of the tube materials according to the invention reside in their specific inactivity in respect to the synthesis gas components. They have only a slight catalytic activity so that there is almost no formation of hydrocarbons by the hydrogenation of carbon monoxide. Besides, they are not attacked by carbon monoxide with formation of carbonyl; this remark is applicable to the iron and nickel contents.

For a fuller understanding of the invention, a comparative example will now be described, in which different tube materials are compared as to their catalytic activity under the same conditions of methanol synthesis.

A synthesis gas composed of

| | |
|---|---|
| $CO_2$ | 4% by volume |
| CO | 10% by volume |
| $H_2$ | 66% by volume |
| $CH_4$ | 10% by volume |
| $N_2$ + Ar | 10% by volume | is reacted under a pressure of 60 kilograms per square centimeter above atmospheric pressure and at a temperature of 250° C. in contact with a known catalyst, prepared as described in U.S. Pat. No. 2,014,883, which contains 60% Cu, 30% Zn, and 10% Cr, at a space velocity of 10,000 standard cubic meters of synthesis gas per cubic meter of catalyst and per hour. 1960 cubiccentimeters of catalyst are contained in a tube which is 1 meter long and 0.05 meter in diameter and which is surrounded by a pressure water jacket. The water contained in the pressure jacket takes up the heat produced by the methanol reaction and high-pressure steam is thus formed.

In all cases, 0.062 kilogram methanol per standard cubic meter of synthesis gas was formed, on an average, under these conditions. The deviation of the yield from this average was only slight. The methanol products differed substantially, however, in their hydrocarbon content.

(a) The catalyst tube consisted of a plain carbon steel having the specification 0.17% by weight C, 0.25% by weight Si, 0.5% by weight Mn (Material No. 1.0061 according to DIN 17007). The methanol product contained 2280 ppm liquid hydrocarbons composed as follows:

| | |
|---|---|
| Pentane | 100 ppm |
| hexane | 360 ppm |
| heptane | 480 ppm |
| octane | 430 ppm |
| nonane | 390 ppm |
| decane | 520 ppm |

(b) The catalyst tube consisted of a low-carbon chromium steel containing 0.1% by weight C and 17% by weight Cr (Material No. 1.4016 according to DIN 17007). The raw methanol product contained 107 ppm hydrocarbons composed as follows:

| | |
|---|---|
| Pentane | 30 ppm |
| hexane | 12 ppm |
| heptane | 10 ppm |
| octane | 35 ppm |
| nonane | 10 ppm |
| decane | 10 ppm |

(c) The catalyst tube consisted of a chromium-nickel steel having a mixed austenitic-ferritic structure and containing 19% by weight chromium and 5% nickel (Material No. $\times$3CrNi 1805 according to DIN 17006). The raw methanol product contained 99 ppm liquid hydrocarbons composed as follows:

| | |
|---|---|
| Pentane | 30 ppm |
| hexane | 10 ppm |

|  |  |
|---|---|
| heptane | 10 ppm |
| octane | 30 ppm |
| nonane | 10 ppm |
| decane | 9 ppm |

(d) The catalyst-holding tube consisted of an austenitic steel which contained 0.1% by weight C, 18% by weight Cr, 10% by weight Ni (Material No. 1.4541 according to DIN 17007). The raw methanol product contained 62 ppm hydrocarbons composed as follows:

|  |  |
|---|---|
| Pentane | 20 ppm |
| hexane | 10 ppm |
| heptane | 10 ppm |
| octane | 10 ppm |
| nonane | 5 ppm |
| decane | 7 ppm |

(e) Catalyst tubes made from a composite material consisting of a shell tube made from a plain carbon steel to one of the above-mentioned specifications (No. 1.0061 and No. 1.5415 according to DIN 17007) and lined on the inside with copper or a Cu-Zn alloy, could be used in the comparison test to produce a raw methanol which contained less than 90 ppm liquid hydrocarbons.

These experiments confirm the experience that in reactor structure in which a catalytic activity of the reactor material need not be expected, the hydrocarbon content of the raw methanol cannot be lowered much below 100 ppm.

What is claimed is:

1. In a reactor for producing methanol by the reaction of synthesis gases containing the oxides of carbon and hydrogen, said reactor comprising a plurality of catalyst tubes positioned within a shell containing boiling water under pressure, a synthesis gas inlet communicating with one end of said plurality of catalyst tubes, a product gas outlet communicating with the other end of said plurality of catalyst tubes, a water inlet in said shell, a steam outlet in said shell, and copper-containing catalyst positioned within said catalyst tubes, wherein the improvement comprises said catalyst tubes being composed of a steel of mixed austenitic-ferritic structure and containing 10–30% by weight chromium.

* * * * *